(12) United States Patent
Huang

(10) Patent No.: US 7,323,319 B2
(45) Date of Patent: Jan. 29, 2008

(54) RNA CONTAINING COENZYMES, BIOTIN, OR FLUOROPHORES, AND METHODS FOR THEIR PREPARATION AND USE

(75) Inventor: Faqing Huang, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 563 days.

(21) Appl. No.: 10/250,029

(22) Filed: May 29, 2003

(65) Prior Publication Data

US 2004/0241649 A1   Dec. 2, 2004

(51) Int. Cl.
C12P 19/34 (2006.01)
C12P 19/32 (2006.01)
C07H 21/02 (2006.01)
C07H 21/04 (2006.01)
C12N 9/00 (2006.01)
C12N 15/00 (2006.01)

(52) U.S. Cl. .................. 435/91.21; 536/23.1; 536/24.1; 536/24.3; 536/24.5; 435/91.3; 435/91.5; 435/183; 435/320.1

(58) Field of Classification Search .................. None
See application file for complete search history.

(56) References Cited

OTHER PUBLICATIONS

Helm et al., 1999, RNA 5:618-621.*
Malygin et al., 1979, FEBS Lett. 102:51-54.*
Conaway et al., 1988, J. Biological Chemistry 263:2962-2968.*
Bunick et al, Cell., 1982, 877-886.*
Smagowicz et al., 1981, Nuclei acid research 10:2397-2410.*
Yarbrough et al., 1979, J. Biol. Chem. 254:12069-12073.*
Groner., 1978, Biochemistry 17:977-982.*
Huang et al, 31(3): e8 (pp. 1-8), 2003.*
Huang et al, 32(1): e14 (pp. 1-4), 2004.*
http://www-dept.usm.edu/~chembio/FACULTY/huang.htm; The University of Southern Mississippi; "Faqing Huang;" printed May 12, 2003.
http://ocean.otr.usm.edu/~fhuan2/; "Faqing Huang Lab Homepage," printed May 12, 2003.
http://ocean.otr.usm.edu/~fhuan2/HuangPubs.htm; "Faqing Huang Publications;" printed May 12, 2003.
http://ocean.otr.usm.edu/~fhuang2/HuangResearch.htm; "Faqing Huang Lab Research;" printed May 12, 2003.
"RNA-Catalyzed CoA, NAD, and FAD Synthesis from Phosphopantetheine, NMN, and FMN;" Faqing Huang, Charles Walter Bugg, Michael Yarus; Biochemistry 2000, 39, 15548-15555.
"Efficient Incorporation of CoA, NAD and FAD into RNA by in vitro transcription;" Faqing Huang; Nucleic Acids Research, 2003, vol. 31, Oxford University Press 2003.
"Complete Nucleotide Sequence of Bacteriophage T7 DNA and the Locations of T7 Genetic Elements;" John J. Dunn and F. Williams Studier; Journal of Molecular Biology, vol. 166, No. 4, Jun. 5, 1983.
"Analytical Biochemistry; Methods in the Biological Sciences; " Irina D. Pokrovskaya and Vsevolod V. Gurevich; Academic Press, Inc., vol. 220, No. 2, Aug. 1, 1994.
"Olkigoribonucleotide synthesis using T7 RNA polymerase and synthetic DNA templates;" John F. Milligan, Duncan R. Groebem, Gary W. Witherell and Olke C. Uhlenbeck; Nucleic Acids Research; vol. 15, No. 21, 1987.
"Transcription Initiation Site Selection and Abortive Initiation Cycling of Phage SP6 RNA Polymerase;" Sang-Chul Nam and Changwon Kang; The Journal of Biologial Chemistry; vol. 263, No. 34, 1988.
"More Mistakes by T7 RNA Polymerase at the 5' ends of in vitro-transcribed RNAs;" Mark Helm, Herve Brule, Richard Giege; Catherine Florentz; RNA (1999), 5:618-621, Cambridge University Pres. Printed in the USA.
Coleman TM, Wang G, Huang F (2004). Superior 5' homogeneity of RNA from ATP-initiated transcription under the T7 ø2.5 promoter. Nucleic Acids Research. 32(1)e14.

* cited by examiner

Primary Examiner—Sumesh Kaushal
Assistant Examiner—Kelaginamane Hiriyanna
(74) Attorney, Agent, or Firm—Howrey LLP

(57) ABSTRACT

Materials and methods for incorporating adenosine derivatives into the 5' end of transcribed RNA are disclosed. Adenosine derivatives include naturally occurring compounds such as Coenzyme A, NAD, and FAD, as well as various non-naturally occurring compounds. The derivatives can be used to impart desirable properties to the RNA such as fluorescence, the ability to bind to receptors or ligands, and improved catalytic activity. The transcribed RNAs can be used in a variety of applications including nucleic acid detection, designed or random generation of catalytic RNAs, antisense applications, and in the study of RNA structure and function.

8 Claims, 9 Drawing Sheets

(I)

(II)

(III)

(IV)

(V)

(VI)

RNA CONTAINING COENZYMES, BIOTIN, OR FLUOROPHORES, AND METHODS FOR THEIR PREPARATION AND USE

FEDERAL RESEARCH STATEMENT

The government may own rights in the present invention pursuant to grant number MCB9974487 from the National Science Foundation and grant number NAG5-10668 from the National Aeronautics and Space Administration.

BACKGROUND OF INVENTION

1. Field of the Invention

The invention relates to RNA molecules having adenosine derivatives incorporated into the 5' end, and methods and materials for their preparation and use.

2. Description of the Related Art

Coenzymes are a group of small organic molecules with distinct chemical functionalities, which are usually unavailable or insufficient in the side chains of the 20 naturally occurring amino acids. A number of metabolic protein enzymes require coenzymes to act as accessory molecules to provide necessary reactivities. Three common coenzymes, coenzyme A (CoA), nicotinamide adenine dinucleotide (NAD), and flavin adenine dinucleotide (FAD) carry out a variety of acyl group transfer and electron/hydride transfer reactions in metabolism. Although CoA, NAD, and FAD function in very different chemical capacities, they share some surprisingly common structural features: a ribonucleoside adenosine at one end, a chemically functional group (pantetheine, nicotinamide, or riboflavin) at the other, and a pyrophosphate connecting the two groups.

Because the structures and functions of these coenzymes are conserved in all kingdoms, CoA, NAD, and FAD are believed to have existed since the last common ancestor of life on Earth. Furthermore, the fact that all these coenzymes contain an adenosine group, one of the four essential building monomers for RNA, suggests the plausibility of their existence and biological function in a more ancient world. Recently, RNA-catalyzed synthesis of these three coenzymes from their corresponding precursors, phosphopantetheine, nicotinamide mononucleotide (NMN), and flavine mononucleotide (FMN) (4) was demonstrated (Huang, F., et al. *Biochemistry* 39: 15548-15555 (2000)), providing strong experimental evidence of possible coenzyme synthesis and utilization in the RNA world (Gilbert, W. *Nature* 319: 618 (1986)).

Currently known ribozymes, either naturally occurring or isolated in vitro, however, do not these coenzymes to perform chemistries as protein enzymes do. A recent report has demonstrated RNA-catalyzed acyl CoA synthesis (Jadhav, V. R., and Yarus, M. *Biochemistry* 41: 723-729 (2002)), and ribozymes have been isolated capable of catalyzing thioester formation (Coleman, T. M., and Huang, F. *Chem. Biol.*, 9: 1227-1236 (2002)). Yet, RNA catalytic activities involving NAD and FAD redox chemistry have not been shown to be within the functional capacity of RNA. Since the development of in vitro selection (SELEX) (Ellington, A. D., and Szostak, J. W. *Nature* 346, 818-822 (1990); Tuerk, C., and Gold, L. *Science* 249: 505-510 (1990); Robertson, D. L., and Joyce, G. F. *Nature* 344: 467-468 (1990)), numerous artificial ribozymes have been isolated from random RNA libraries (Jaschke, A. *Curr. Opin. Struct. Biol* 11: 321-326 (2001)).

Convenient and efficient in vitro transcription methods have played an important role in the advancement of RNA research by providing easily available RNA with defined sequences. However, all the current methods require a guanosine derivative as the transcription initiator under T3, T7, and SP6 promoters (Milligan, J. F., et al., *Nucleic Acids Res.* 15: 8783-8798 (1987); Pokrovskaya, I. D., and Gurevich, V. V., *Anal. Biochem.* 220: 420-423 (1994)). Although other nucleotides such as adenosine and cytidine derivatives have been shown to be able to initiate transcription with certain sequences (Nam, S. C., and Kang, C. W., *J. Biol. Chem.* 263: 18123-18127 (1988); Helm, M., et al., *RNA* 5: 618-621 (1999)), the initiation sites are not well defined. The yields are low (Nam, S. C., and Kang, C. W., *J. Biol. Chem.* 263: 18123-18127 (1988)), and they usually result from non-templated incorporation or omission of one or two nucleotides (Helm, M., et al., *RNA* 5: 618-621 (1999)).

Development of methods for the preparation of RNA molecules linked to coenzymes and other adenosine derivatives may provide interesting catalysts that have improved or novel properties as compared to current RNA catalysts. Incorporation of fluorophores or biotin at the specific 5' end of RNA results in site-specifically labeled RNA that may be used in RNA structural and functional investigation and nucleic acid detection.

SUMMARY OF INVENTION

Chemical and enzymatic methods for the preparation of RNA molecules covalently linked to coenzymes or other adenosine derivatives are disclosed. An in vitro transcription method has been developed that provides for the covalent incorporation of derivatives into the 5' end of a transcribed RNA molecule.

BRIEF DESCRIPTION OF DRAWINGS

The following figures form part of the present specification and are included to further demonstrate certain aspects of the present invention. The invention may be better understood by reference to one or more of these figures in combination with the detailed description of specific embodiments presented herein.

BRIEF DESCRIPTION OF SEQUENCES

Figure 1A:
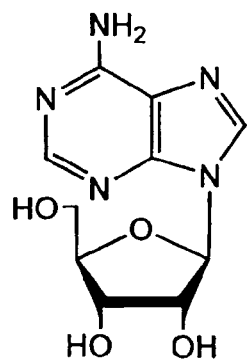
FIGS. 1A-1B shows the structure of adenosine (I), Coenzyme A (II), NAD (III), and FAD (IV).
Figure 1A:
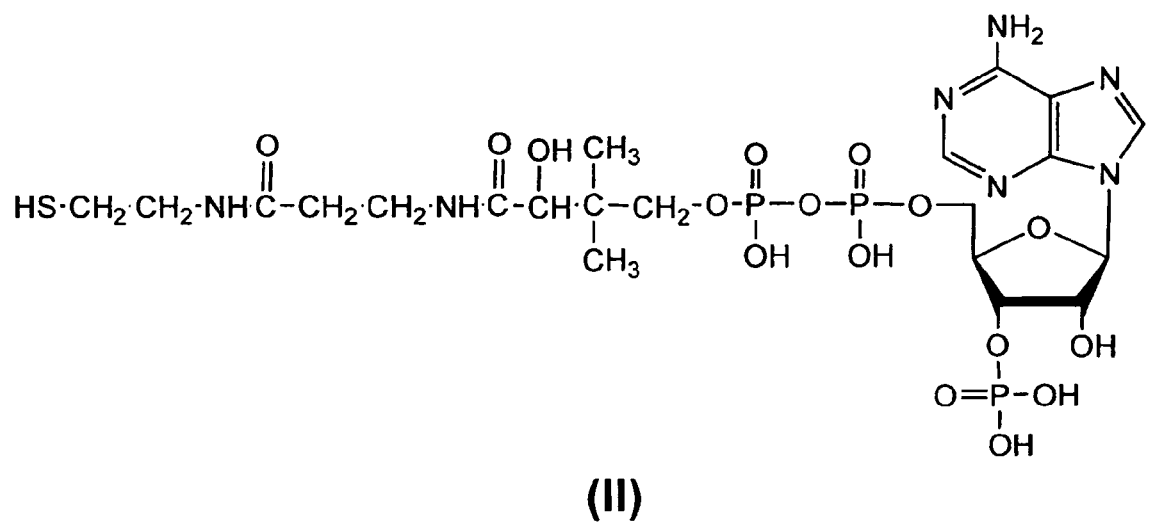
Figure 1B:
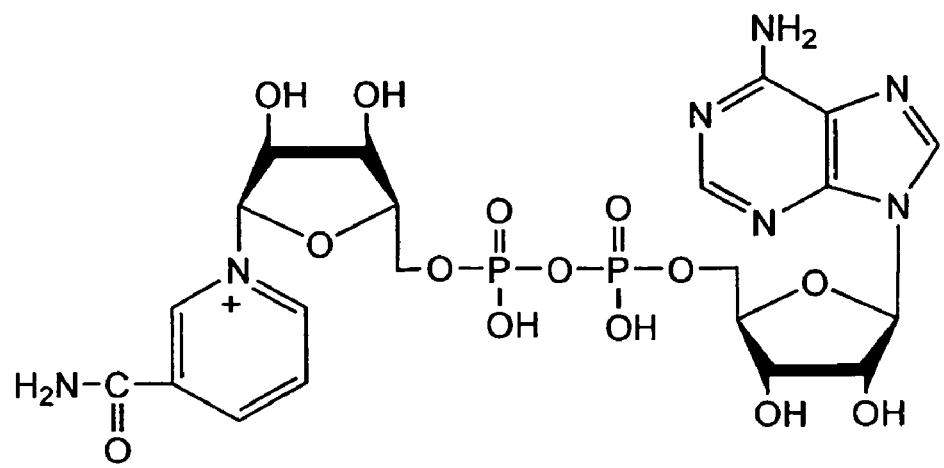
Figure 1B:
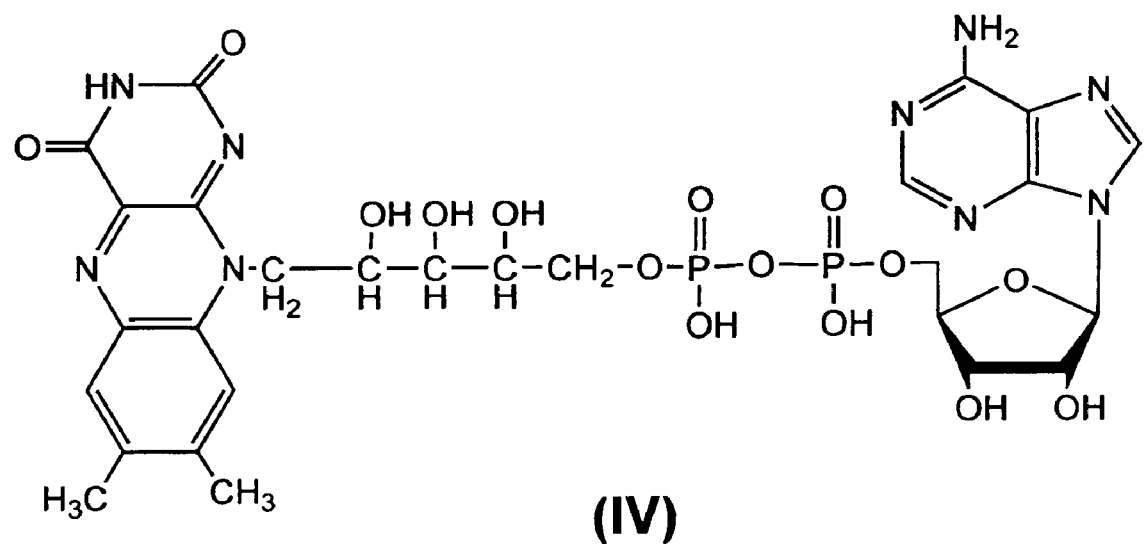

The following sequence listings form part of the present specification and are included to further demonstrate certain aspects of the present invention. The invention may be better understood by reference to one or more of these sequences in combination with the detailed description of specific embodiments presented herein.

SEQ ID NO:1 is the CoES7 ribozyme sequence.
SEQ ID NO:2 is a DNA duplex template oligonucleotide.
SEQ ID NO:3 is a DNA duplex template oligonucleotide.
SEQ ID NO:4 is a RNA sequence transcribed from the DNA duplex template.
SEQ ID NO:5 is a DNazyme sequence.
SEQ ID NO:6 is a T3 promoter sequence.
SEQ ID NO:7 is a T7 class II promoter sequence.
SEQ ID NO:8 is a SP6 promoter sequence.
SEQ ID NO:9 is the reverse complement of SEQ ID NO:7.

DETAILED DESCRIPTION

Currently known ribozymes are RNA molecules selected for their ability to bind a substrate, to catalyze a reaction, or to perform some other selectable activity. In order to use coenzymes (as do many protein enzymes), the RNA molecules would have to additionally bind the coenzyme (s). Covalent coupling of coenzymes to RNA sequences not only eliminates the requirement of coenzyme binding by ribozymes, but may also provide a practical means of selection based on the coenzyme reactivity. The development of a general method of incorporating CoA, NAD, FAD into RNA through in vitro transcription is disclosed herein. This procedure may be used to construct coenzyme-linked RNA libraries for in vitro selection or to prepare coenzyme-coupled specific RNA sequences for other purposes, such as fluorescent labeling and detection of RNA/DNA, investigation of RNA structure, and studying RNA-RNA interaction and RNA-protein interaction.

RNA transcription can be initiated by adenosine derivatives, including ATP, De-P-CoA, NAD, and FAD using a transcription promoter sequence derived from T7 class II promoters. Adenosine can be used to prepare adenosine-initiated RNA with free 5' hydroxyl groups, permitting easy $^{32}$P-labeling of the 5' end of RNA by polynucleotide kinase. Because only the adenosine group is required for recognition by T7 RNA polymerase to initiate transcription, a large number of adenosine derivatives can be used to prepare adenosine derivative-linked RNA. In addition to the three coenzymes (CoA, NAD, and FAD) and various adenosine derivatives described in the Examples below, a variety of biologically active molecules can be linked to the 5'-end of RNA. These include coenzymes S-adenosylcysteine, S-adenosylhomocysteine (AdoHcy), and S-adenosylmethionine (SAM), sugar-containing molecule adenosine 5'-diphosphoglucose (ADPG), and the signaling molecules diadenosine polyphosphates Ap(3)A and Ap(4)A. Chemically modified adenosine derivatives such as fluorescent ATP derivatives may also be used to prepare 5' fluorophore-linked RNA. Similar strategies have been used to prepare 5' fluorophore-linked RNA by guanosine derivatives. While other RNA polymerases such as E. coli RNA polymerase can be used to prepare adenosine derivative-initiated RNA, the well defined T3, T7, and SP6 promoters, high yields of transcription, and easy preparation of these phage RNA polymerases make them attractive for in vitro RNA preparation.

ATP and adenosine derivatives can initiate transcription of any defined sequences with high efficiency, thereby providing researchers with choices of different 5'-ends of RNA. High yields of adenosine derivative-initiated random RNA libraries can be achieved, reaching as high as 100 mg RNA per 100 mL transcription under standard transcription conditions in preliminary experiments. Up to 300 copies of 50 nt RNA molecules can be synthesized from a single DNA template according to preliminary results.

In transcription where an adenosine derivative (R-A) other than ATP is present, both normal RNA (pppRNA) and adenosine derivative-linked RNA (R-ARNA) are produced. Although high concentrations of adenosine derivatives (such as De-P-CoA, NAD, and FAD) lead to high relative yields of R-RNA over total RNA (pppRNA and R-RNA), total RNA yields may decrease at high concentrations of adenosine derivatives. To balance the total RNA yields and relative yields of adenosine derivative-linked RNA, transcription in the presence of 1 mM each of the four nucleoside triphosphates and 4 mM of an adenosine derivative can be performed. However, if higher relative yields of adenosine derivative-linked RNA are desired and lower total RNA yields are acceptable, higher concentrations of adenosine derivatives or lower concentrations of ATP may be used. At higher than 8 mM of adenosine derivative concentrations, total RNA yields can be significantly lower. At 0.2-0.5 mM ATP and 4 mM De-P-CoA, transcription produces over 50% CoA-RNA with about 20-50% reduction in total RNA yields. Optimization of transcription conditions such as magnesium concentration may improve the total RNA yield and relative yield of adenosine derivative-linked RNA.

The fluorescence property of FAD-RNA can be used to investigate RNA structure and function relationship. The defined 5' end location of the fluorophore FAD and easy preparation of FAD-RNA by the in vitro transcription methods disclosed herein should be advantageous for structural investigation of RNA by steady-state fluorescence spectroscopy. The lifetime of the fluorophore FAD in FAD-RNA may change and correlate with its chemical environment, providing a sensor for RNA folding and conformation through time-resolved fluorescence spectroscopy. Furthermore, another fluorophore (either a donor or an acceptor) can be introduced to other locations in the RNA to allow investigation of spatial arrangement of the RNA around its 5' end by fluorescence resonance energy transfer (FRET). For small RNA fragments, fluorophores can be added at specific locations by chemical synthesis. However, introduction of a specific chemical group (including a fluorophore) at a defined location in relatively large RNA may involve multiple steps of transcription, chemical synthesis, and ligation. With an appropriate fluorescence donor or acceptor, FAD-initiated transcription can significantly reduce the number of steps needed to prepare RNA suitable for a broad range of FRET studies.

FAD-RNA may find other applications such as fluorescence detection of complementary RNA/DNA sequences. 5' FAD-labeled different RNA sequences can be conveniently synthesized by the in vitro transcription methods disclosed herein, to allow detection of large number of different RNA/DNA sequences.

In addition, the reduced form of NAD (i.e., NADH) is also highly fluorescent. Therefore, NADH-RNA may find wide range of applications as discussed above. NADH and FAD have different spectral properties and lifetimes and may respond differently to their RNA environment. FAD-RNA and NADH-RNA may accordingly be combined in RNA structural investigation by fluorescence spectroscopy.

Aspects of the invention include nucleic acid molecules, methods for their preparation, and methods for their use.

Nucleic Acid Molecules

One embodiment of the invention includes RNA molecules containing adenosine derivatives covalently attached to the 5' end of the RNA molecule. The RNA molecule can generally have any RNA sequence. The length of the RNA sequence can generally be any number of bases. For example, the RNA sequence can be at least about 5 bases, at least about 10 bases, at least about 20 bases, at least about 30 bases, at least about 40 bases, at least about 50 bases, at least about 60 bases, at least about 70 bases, at least about 80 bases, at least about 90 bases, at least about 100 bases, at least about 200 bases, at least about 300 bases, at least about 400 bases, at least about 500 bases, at least about 600 bases, at least about 700 bases, at least about 800 bases, at least about 900 bases, at least about 1000 bases, at least about 2000 bases, and so on. There is no practical upper limit to the length of the RNA sequence, as it is dependent primarily upon the length of the template nucleic acid sequence used in its preparation (or upon the synthetic method used). The RNA molecule can be isolated, or can be present as a mixture of RNA molecules.

The adenosine derivative can generally be any adenosine derivative, including coenzymes. Examples of the adenosine derivatives include coenzyme A ("CoA"), nicotinamide adenine dinucleotide ("NAD"), flavin adenine dinucleotide ("FAD"), S-(5'-adenosyl)-cysteine, S-(5'-adenosyl)-homocysteine, S-(5'-adenosyl)-methionine, adenosine 5'-diphosphoglucose, adenosine 5'-(α,β-methylene)diphosphate, adenosine 5'-(β,γ-imido)triphosphate, adenosine 5'-triphosphate γ-(1-(2-nitrophenyl)ethyl) ester, and 5'-p-fluorosulfonylbenzoyladenosine. The adenosine derivatives can be modified at the 5' position, the N6 position, or both.

The adenosine derivative can include additional chemical functional groups that can be used for further post-transcriptional modification. For example, the adenosine derivative may have a thiol group (—SH), an amine group (—$NH_2$, —NHR, —$NR_2$), a phosphorothioate group (—O—P(S)$O_2$), a carboxylic acid group (—$CO_2H$), a hydroxyl group (—OH), a carbonyl group (C=O), an aldehyde group (—CHO), an amide group (CHN), or a protected functional group, any of which could be used in further chemical reactions.

Additional modifications can include covalently attaching an amino acid, peptide, or protein to the transcribed RNA molecule. The attaching step is presently preferred to include the formation of an amide bond between a primary amine group in the adenosine derivative and a carboxylate group in the amino acid, peptide, or protein. The attaching step can be performed on the adenosine derivative prior to its incorporation into the transcribed RNA molecule, or after its incorporation. It is presently preferred that the attaching step be performed on the adenosine derivative prior to its incorporation into the transcribed RNA molecule.

Adenosine Derivative Molecules

Adenosine derivatives can generally be any adenosine derivative such as a coenzyme. Examples of coenzymes include coenzyme A ("CoA"; $C_{21}H_{36}N_7O_{16}P_3S$), nicotinamide adenine dinucleotide ("NAD"; $C_{21}H_{27}N_7O_{14}P_2$), flavin adenine dinucleotide ("FAD"; $C_{27}H_{31}N_9O_{15}P_2Na_2$), S—(5'-adenosyl)-cysteine ($C_{13}H_{18}N_6O_5S$), S—(5'-adenosyl)-homocysteine ($C_{14}H_{20}N_6O_5S$), S—(5'-adenosyl)-methionine ($C_{15}H_{23}N_6O_5SCl$, chloride), adenosine 5'-diphosphoglucose ($C_{16}H_{23}N_5O_{15}P_2Na_2$), adenosine 5'-(α,β-methylene) diphosphate ($C_{11}H_{17}N_5O_9P_2$), adenosine 5'-(β,γ-imido)triphosphate ($C_{10}H_{17}N_6O_{12}P_3$), adenosine 5'-triphosphate γ-(1-(2-nitrophenyl)ethyl) ester ($C_{18}H_{23}N_6O_{15}P_3$), 5'-p-fluorosulfonylbenzoyladenosine ($C_6H_4FN_3O_3S$), adenosine 5'-O-thiomonophosphate ($C_{10}H_{12}N_5O_6P$) adenosine 5'-[β-thio]diphosphate ($C_{10}H_{12}N_5P_2$ S), and adenosine 5'-[γ-thio]triphosphate ($C_{10}H_{12}N_5O_{12}P_3S$).

The adenosine derivatives can be modified at the 5' position, the N6 position, or both. Adenosine derivatives can generally be prepared by any acceptable synthetic chemical method or enzymatic method.

Adenosine 5'-(ω-amino-linker) phosphoramidate molecules can be prepared by contacting a diamine, AMP, and EDAC. The diamine can generally be any diamine. Diamines include ethylenediamine (EDA), 1,4-butanediamine (BDA), 1,6-hexanediamine (HDA), 2,2'-oxydiethylamine (ODEA), 2,2'-(ethylenedioxy)diethylamine (EDODEA), and 4,7,10-trioxa-1,13-tridecanediamine (TOTDDA). These diamines provide linkers of $(CH_2)_2$, $(CH_2)_4$, $(CH_2)_6$, $C_2H_4OC_2H_4$, and $C_3H_6OC_2H_4OC_2H_4OC_3H_6$ respectively. Additional diamines (and polyamines) such as spermidine ($NH_2(CH_2)_3NH(CH_2)_4NH_2$), spermine, ($NH_2(CH_2)_3NH(CH_2)_4NH(CH_2)_3NH_2$), polyethylene glycol diamines ($H_2N$-PEG-$NH_2$), 1,4-bis(3-aminopropoxy) butane ($H_2N(CH_2)_3O(CH_2)_4 O(CH_2)_3NH_2$), bis(3-aminopropyl)amine($H_2N(CH_2)_3NH(CH_2)_3NH_2$), tris(2-aminoethyl)amine(N($CH_2CH_2NH_2)_3$), 1,8-diaminooctane ($H_2N(CH_2)_8NH_2$), 1,10-diaminodecane ($H_2N(CH_2)_{10}NH_2$), and 1,12-diaminododecane ($H_2N(CH_2)_{12}NH_2$), can also be used.

Figure 2:
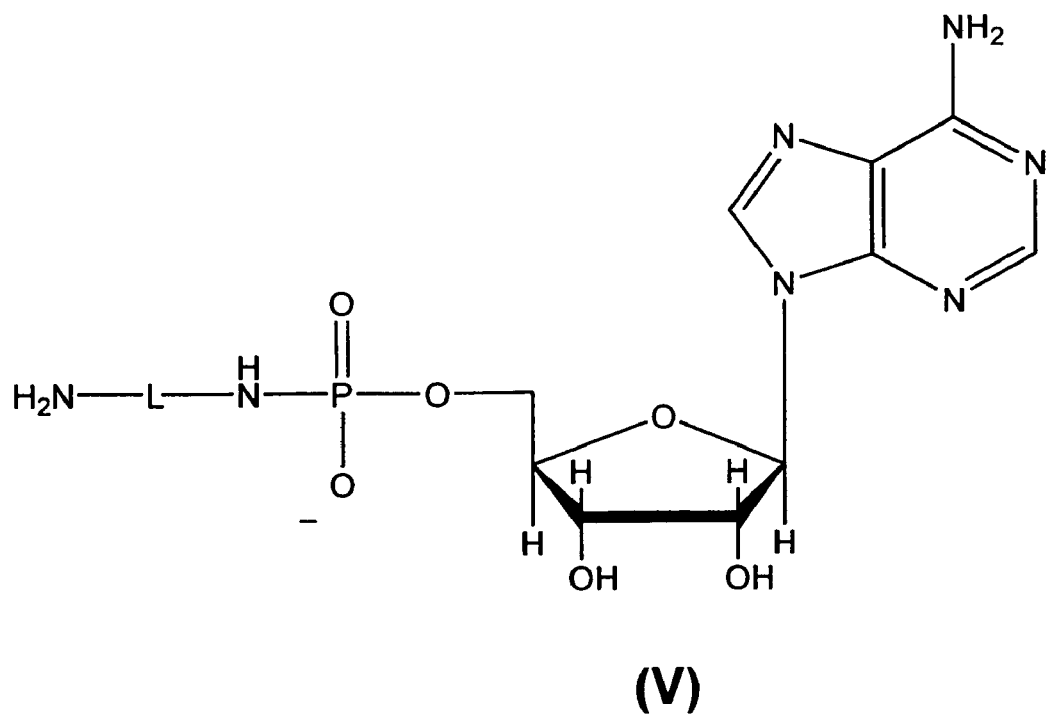
FIG. 2 shows the structure of an adenosine 5'-(ω-amino-linker) phosphoramidate (V) and an N6-(ω-amino-linker) adenosine 5'-monophosphate (VI).
Figure 2:
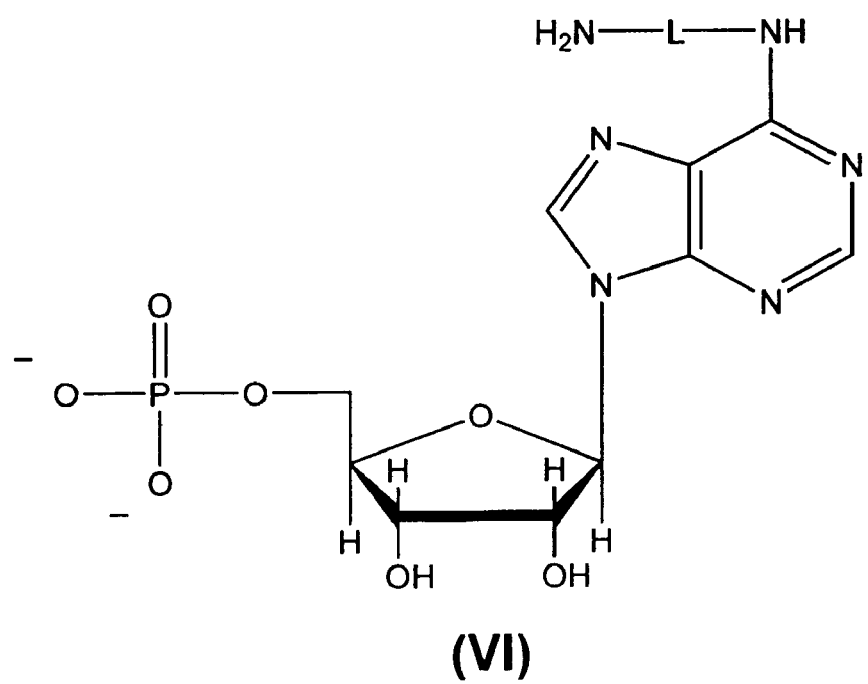
Figure 3:
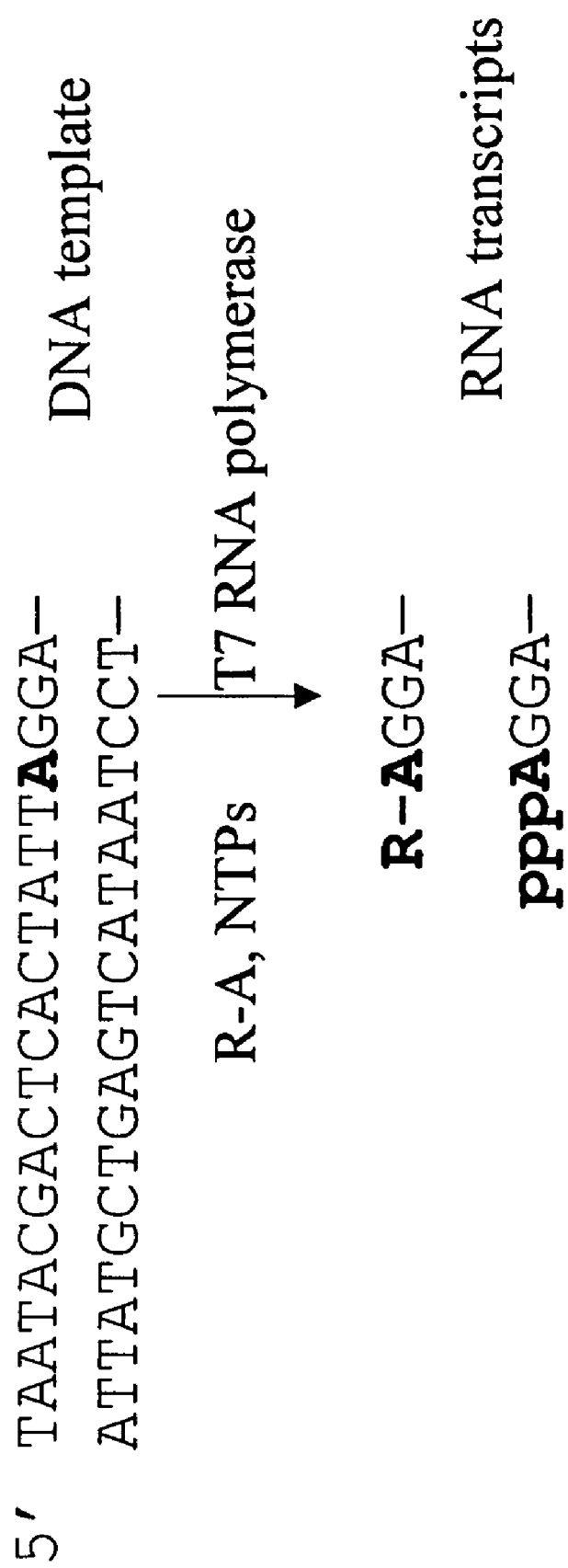
FIG. 3 shows the production of RNA transcripts incorporating adenosine derivatives using the T7 Class II RNA Polymerase promoter (φ 2.5). R-A represents an adenosine derivative; NTPs represents a mixture of ATP, UTP, CTP, and GTP. The top sequence is SEQ ID NO:7, and the bottom sequence is SEQ ID NO:9.

These adenosine 5'-(ω-amino-linker) phosphoramidate molecules can be generically represented by structure (V) in FIG. 2. In the structure, linker L can generically be any alkyl, alkoxy, alkoxy alkyl, alkylamine, or polyalkylamine group. Specific examples include adenosine 5'-aminoethyl phosphoramidate (5'-EDA-AMP), adenosine 5'-(4-aminobutyl) phosphoramidate (5'-BDA-AMP), adenosine 5'-(6-aminohexyl) phosphoramidate (5'-HDA-AMP), adenosine 5'-(2-aminoethoxyethyl) phosphoramidate (5'-ODEA-AMP), adenosine 5'-(3,6-dioxa-8-aminooctyl) phosphoramidate (5'-EDODEA-AMP), and adenosine 5'-(4,7,10-trioxa-13-aminotridecyl) phosphoramidate (5'-TOTDDA-AMP).

Adenosine 5'-(ω-sulfhydryl-linker) phosphoramidate molecules can be prepared by contacting an aminothiol, AMP, and EDAC. The aminothiol can generally be any molecule containing a free amino group and a free sulfhydryl group. Aminothiols include cysteamine and carboxyl group-protected cysteine.

The adenosine 5'-(ω-amino-linker) phosphoramidate molecules can be further reacted with an activated group to modify the linker terminal amino group. For example, succinimide esters can be used to add additional functional moieties. One example of this concept is reaction with 5 (6)-carboxyfluorescein N-hydroxysuccinimide ester (5(6)-FAM-SE) to produce fluorescein derivatives. Carboxyfluorescein is commonly obtained as a mixture of 5- and 6-isomers, although either can be used individually. A list of example products includes 5'-FAM-EDA-AMP, 5'-FAM-BDA-AMP, 5'-FAM-HDA-AMP, 5'-FAM-ODEA-AMP, 5'-FAM-EDODEA-AMP, and 5'-FAM-TOTDDA-AMP. Similarly, biotin N-hydroxysuccinimide ester (biotin-SE) can be used to produce biotinylated derivatives. A list of example products include 5'-biotin-HDA-AMP, 5'-biotin-EDODEA-AMP, and 5'-biotin-TOTDDA-AMP.

The adenosine 5'-(ω-sulfhydryl-linker) phosphoramidate molecules can be further reacted with an activated group to modify the linker terminal thiol group. For example, haloacetamide, halide, and maleimide derivatives can be used to add additional functional moieties. One example of this concept is reaction with fluorescein maleimide, or fluorescein bromoacetamide to produce fluorescein derivatives of adenosine. Biotin derivatives of maleimide or haloacetamide can be used to produce biotinylated derivatives of adenosine.

Adenosine thiophosphate molecules (adenosine 5'-O-thiomonophosphate, adenosine 5'-[β-thio]diphosphate, adenosine 5'-[γ-thio]triphosphate) can also be reacted with an activated group to modify the thiophosphate group. For example, haloacetamide, halide, and maleimide derivatives can be used to add additional functional moieties. One example of this concept is reaction with fluorescein maleimide, or fluorescein bromoacetamide to produce fluorescein derivatives of adenosine. Biotin derivatives of maleimide or haloacetamide can be used to produce biotinylated derivatives of adenosine.

N6-(ω-amino-linker) adenosine 5'-monophosphate can be prepared by contacting 6-chloropurine riboside first with $POCl_3$ then water to produce 6-chloropurine riboside 5'-monophosphate. This intermediate can be reacted with a diamine to produce an N6-(ω-amino-linker) adenosine 5'-monophosphate. Diamines include ethylenediamine (EDA), 1,4-butanediamine (BDA), 1,6-hexanediamine (HDA), 2,2'-oxydiethylamine (ODEA), 2,2'-(ethylenedioxy)diethylamine (EDODEA), and 4,7,10-trioxa-1,13-tridecanediamine (TOTDDA). These diamines provide linkers of $(CH_2)_2$, $(CH_2)_4$, $(CH_2)_6$, $C_2H_4OC_2H_4$ and $C_3H_6OC_2H_4OC_2H_4OC_3H_6$, respectively. Additional diamines (and polyamines) such as spermidine ($NH_2(CH_2)_3NH(CH_2)_4NH_2$), spermine, ($NH_2(CH_2)_3NH(CH_2)_4NH(CH_2)_3NH_2$), polyethylene glycol diamines ($H_2N$-PEG-$NH_2$), 1,4-bis(3-aminopropoxy)butane ($H_2N(CH_2)_3O(CH_2)_4O(CH_2)_3NH_2$), bis(3-aminopropyl)amine($H_2N(CH_2)_3NH(CH_2)_3NH_2$), tris(2-aminoethyl)amine($N(CH_2CH_2NH_2)_3$), 1,8-diaminooctane ($H_2N(CH_2)_8NH_2$), 1,10-diaminodecane ($H_2N(CH_2)_{10}NH_2$), and 1,12-diaminododecane ($H_2N(CH_2)_{12}NH_2$), can also be used.

N6-(ω-amino-linker) adenosine 5'-diphosphate and N6-(ω-amino-linker) adenosine 5'-triphosphate can be prepared by contacting 6-chloropurine riboside 5'-diphosphate or 6-chloropurine riboside 5'-triphosphate with a diamine to produce an N6-(ω-amino-linker) adenosine 5'-diphosphate or N6-(ω-amino-linker) adenosine 5'-triphosphate. Diamines may include ethylenediamine (EDA), 1,4-butanediamine (BDA), 1,6-hexanediamine (HDA), 2,2'-oxydiethylamine (ODEA), 2,2'-(ethylenedioxy)diethylamine (EDODEA), and 4,7,10-trioxa-1,13-tridecanediamine (TOTDDA). These diamines provide linkers of $(CH_2)_2$, $(CH_2)_4$, $(CH_2)_6$, $C_2H_4OC_2H_4$, and $C_3H_6OC_2H_4OC_2H_4OC_3H_6$ respectively. Additional diamines such as spermidine ($NH_2(CH_2)_3NH(CH_2)_4NH_2$), spermine, ($NH_2(CH_2)_3NH(CH_2)_4NH(CH_2)_3NH_2$), polyethylene glycol diamines ($H_2N$-PEG-$NH_2$), 1,4-bis(3-aminopropoxy)butane ($H_2N(CH_2)_3O(CH_2)_4O(CH_2)_3NH_2$), bis(3-aminopropyl)amine($H_2N(CH_2)_3NH(CH_2)_3NH_2$), tris(2-aminoethyl)amine($N(CH_2CH_2NH_2)_3$), 1,8-diaminooctane ($H_2N(CH_2)_8NH_2$), 1,10-diaminodecane ($H_2N(CH_2)_{10}NH_2$), and 1,12-diaminododecane ($H_2N(CH_2)_{12}NH_2$), can also be used.

N6-(ω-sulfhydryl-linker) adenosine 5'-monophosphate molecules, N6-(ω-sulfhydryl-linker) adenosine 5'-diphosphate molecules, and N6-(ω-sulfhydryl-linker) adenosine 5'-triphosphate molecules can be prepared by contacting an aminothiol with 6-chloropurine riboside 5'-monophosphate, 6-chloropurine riboside 5'-diphosphate or 6-chloropurine riboside 5'-triphosphate to produce an N6-(ω-sulfhydryl-linker) adenosine 5'-monophosphate, N6-(ω-sulfhydryl-linker) adenosine 5'-diphosphate, or N6-(ω-sulfhydryl-linker) adenosine 5'-triphosphate.

N6-(ω-amino-linker) adenosine 5'-O-thiomonophosphate, N6-(ω-amino-linker) adenosine 5'-[β-thio]diphosphate, and N6-(ω-amino-linker) adenosine 5'-[γ-thio]triphosphate can be prepared by contacting 6-chloropurine riboside 5'-O-thiomonophosphate, 6-chloropurine riboside 5'-[β-thio]diphosphate, or 6-chloropurine riboside 5'-[γ-thio]triphosphate with a diamine to produce an N6-(ω-amino-linker) adenosine 5'-O-thiomonophosphate, N6-(ω-amino-linker) adenosine 5'-[β-thio]diphosphate, or N6-(ω-amino-linker) adenosine 5'-[β-thio]diphosphate. Diamines may include ethylenediamine (EDA), 1,4-butanediamine (BDA), 1,6-hexanediamine (HDA), 2,2'-oxydiethylamine (ODEA), 2,2'-(ethylenedioxy)diethylamine (EDODEA), and 4,7,10-trioxa-1,13-tridecanediamine (TOTDDA). These diamines provide linkers of $(CH_2)_2$, $(CH_2)_4$, $(CH_2)_6$, $C_2H_4OC_2H_4$, and $C_3H_6OC_2H_4OC_2H_4OC_3H_6$ respectively. Additional diamines such as spermidine ($NH_2(CH_2)_3NH(CH_2)_4NH_2$), spermine, ($NH_2(CH_2)_3NH(CH_2)_4NH(CH_2)_3NH_2$), polyethylene glycol diamines ($H_2N$-PEG-$NH_2$), 1,4-bis(3-aminopropoxy)butane ($H_2N(CH_2)_3O(CH_2)_4O(CH_2)_3NH_2$), bis(3-aminopropyl)amine($H_2N(CH_2)_3NH(CH_2)_3NH_2$), tris(2-aminoethyl)amine($N(CH_2CH_2NH_2)_3$), 1,8-diaminooctane ($H_2N(CH_2)_8NH_2$), 1,10-diaminodecane ($H_2N(CH_2)_{10}NH_2$), and 1,12-diaminododecane ($H_2N(CH_2)_{12}NH_2$), can also be used.

These N6-(ω-amino-linker) adenosine 5'-monophosphate molecules can be generically represented by structure (VI) in FIG. 2. In the structure, linker L can generically be any alkyl, alkoxy, alkoxy alkyl, alkylamine, or polyalkylamine group (such as described above). Specific examples include N6-aminoethyl adenosine 5'-monophosphate (N6-EDA-AMP), N6-(4-aminobutyl) adenosine 5'-monophosphate (N6-BDA-AMP), N6-(6-aminohexyl) adenosine 5'-monophosphate (N6-HDA-AMP), N6-(2-aminoethyl) adenosine 5'-monophosphate (N6-ODEA-AMP), N6-(3,6-dioxa-8-aminooctyl) adenosine 5'-monophosphate (N6-EDODEA-AMP), and N6-(4,7,10-trioxa-13-aminotridecyl) adenosine 5'-monophosphate (N6-TOTDDA-AMP).

The N6-(ω-amino-linker) adenosine 5'-monophosphate molecules can be further reacted with an activated group to modify the linker terminal amino group. For example, succinimide esters can be used to add additional functional moieties. One example of this concept is reaction with 5(6)-carboxyfluorescein N-hydroxysuccinimide ester (5(6)-FAM-SE) to produce fluorescein derivatives. Carboxyfluorescein is commonly obtained as a mixture of 5- and 6-isomers, although either can be used individually. A list of example products includes N6-FAM-EDA-AMP, N6-FAM-BDA-AMP, N6-FAM-HDA-AMP, N6-FAM-ODEA-AMP, N6-FAM-EDODEA-AMP, and N6-FAM-TOTDDA-AMP. Similarly, biotin N-hydroxysuccinimide ester (biotin-SE) can be used to produce biotinylated derivatives. A list of example products include N6-biotin-BDA-AMP, N6-biotin-HDA-AMP, N6-biotin-EDODEA-AMP, and N6-biotin-TOTDDA-AMP.

The N6-(ω-amino-linker) adenosine 5'-diphosphate molecules and N6-(ω-amino-linker) adenosine 5'-triphosphate molecules can be further reacted with an activated group to modify the linker terminal amino group. For example, N-hydroxysuccinimide esters can be used to add additional functional moieties. One example of this concept is reaction with 5(6)-carboxyfluorescein N-hydroxysuccinimide ester (5(6)-FAM-SE) to produce fluorescein derivatives.

The N6-(ω-sulfhydryl-linker) adenosine 5'-monophosphate molecules, N6-(ω-sulfhydryl-linker) adenosine 5'-diphosphate molecules, and N6-(ω-sulfhydryl-linker) adenosine 5'-triphosphate molecules can be further reacted with an activated group to modify the linker terminal thiol group. For example, haloacetamide, halide, and maleimide derivatives can be used to add additional functional moieties. One example of this concept is reaction with fluorescein maleimide, or fluorescein bromoacetamide to produce fluorescein derivatives of adenosine. Biotin derivatives of maleimide or haloacetamide can be used to produce biotinylated derivatives of adenosine.

The N6-(ω-amino-linker) adenosine 5'-O-thiomonophosphate, N6-(ω-amino-linker) adenosine 5'-[β-thio]diphosphate, and N6-(ω-amino-linker) adenosine 5'-[γ-thio]triphosphate can also be reacted with an activated group to modify the thiophosphate group. For example, haloacetamide, halide, and maleimide derivatives can be used to add additional functional moieties. One example of this concept is reaction with fluorescein maleimide, or fluorescein bromoacetamide to produce fluorescein derivatives of adenosine. Biotin derivatives of maleimide or haloacetamide can be used to produce biotinylated derivatives of adenosine.

AMP 5'-derivatives of amino acids, neurotransmitters (such as serotonin, dopamine, epinephrine (adrenalin), tyamine, histamine), amino acid-sugars (such as glucose cysteine) peptides, and proteins can be prepared by contacting AMP with the amino-containing compound (carboxy groups preferably should be protected to avoid reaction with EDAC) and EDAC to produce a 5'-amino acid-, neurotransmitter-, amino acid-sugar-, peptide-, or protein-derivative of AMP.

AMP, ADP, and ATP N6-derivatives of amino acids, neurotransmitters (such as serotonin, dopamine, epinephrine (adrenalin), tyamine, histamine), amino acid-sugars (such as glucose cysteine) peptides, and proteins can be prepared by contacting AMP, ADP, and ATP with the amino-containing compound to produce an N6-amino acid-, neurotransmitter-, amino acid-sugar-, peptide-, or protein-derivative of AMP, ADP, or ATP.

Kits

An additional embodiment of the invention is related to kits useful for the preparation of the above described RNA molecules. The kits can comprise reagents, enzymes, nucleic acid templates, one or more containers, buffers, solvents, instruction protocols, purification materials, positive and negative controls, standards, and so on.

An example of such a kit can comprise a RNA polymerase enzyme, one or more of the previously discussed adenosine derivatives, ATP, UTP, GTP, and CTP.

Methods of Preparation of RNA Molecules

Another aspect of the invention relates to methods of preparing RNA molecules having adenosine derivatives or coenzymes at their 5' terminal end. Generally, the method comprises providing a DNA template comprising a RNA polymerase promoter sequence; contacting the DNA template, an RNA polymerase enzyme, an adenosine derivative, ATP, UTP, GTP, and CTP to prepare a reaction mixture; and incubating the reaction mixture under conditions suitable for RNA transcription to prepare RNA molecules. It is presently preferred that the method is an in vitro enzymatic method.

The DNA template can generally be any DNA template. The DNA template can be single stranded or double stranded. The length of the DNA sequence can generally be any number of bases or base pairs. For example, the DNA sequence can be at least about 5 bases, at least about 10 bases, at least about 20 bases, at least about 30 bases, at least about 40 bases, at least about 50 bases, at least about 60 bases, at least about 70 bases, at least about 80 bases, at least about 90 bases, at least about 100 bases, at least about 200 bases, at least about 300 bases, at least about 400 bases, at least about 500 bases, at least about 600 bases, at least about 700 bases, at least about 800 bases, at least about 900 bases, at least about 1000 bases, at least about 2000 bases, and so on. There is no practical upper limit to the length of the DNA sequence. The DNA sequence can be a single DNA sequence, or a mixture of DNA sequences.

It is presently preferred that the promoter sequence be the T7 Class II promoter sequence (5'-TAATACGACTCAC-TATTAGGAG-3'; SEQ ID NO:7). It is currently preferred that the RNA polymerase enzyme is the T7 RNA polymerase enzyme.

The adenosine derivative can be any adenosine derivative or coenzyme discussed above. The reaction mixtures typically will contain ATP, UTP, GTP, and CTP in order to produce a transcribed RNA molecule containing A, U, G, and C. It is possible that some DNA templates may lack one or more of the four bases. In such a case, one or more of ATP, UTP, GTP, and CTP could be omitted. For example, if the DNA template to be transcribed contained only A, G, and C (i.e. no T), then UTP could be omitted from the reaction mixture as the transcribed RNA would contain only A, G, and C.

The reaction mixture can further comprise buffers, surfactants, salts, RNase inhibitors, and other common molecular biology reagents. Incubation under conditions suitable for RNA transcription largely involves selection of buffer, pH, time, and temperature conditions according to the activity requirements of the RNA polymerase enzyme according to the manufacturer's protocols. For example, T7 RNA polymerase can be used with a solution of 40 mM Tris (pH 8.0), 6 mM $MgCl_2$, 2 mM spermidine, 0.01% Triton X-100, 5 mM DTT, and 0.2 unit/μL RNase inhibitor. Incubation can be performed for about two hours to about four hours at a temperature of about 37° C., or according to the enzyme manufacturer's protocols.

In order to prepare a radiolabelled RNA molecule, the reaction mixture can further comprise radioactive components such as $[\alpha\text{-}^{32}P]ATP$, $[\alpha\text{-}^{32}P]GTP$, $[\alpha\text{-}^{32}P]CTP$, $[\alpha\text{-}^{32}P]UTP$, $[\alpha\text{-}^{35}S]ATP$, $[\alpha\text{-}^{35}S]GTP$, $[\alpha\text{-}^{35}S]CTP$, and $[\alpha\text{-}^{35}S]UTP$.

The method can further comprise covalently attaching amino acids, neurotransmitters (such as serotonin, dopamine, epinephrine (adrenalin), tyamine, histamine), amino acid-sugars (such as glucose cysteine) peptides, and proteins to the RNA molecule as discussed above. The attaching step can be performed on the adenosine derivative prior to its incorporation into the transcribed RNA molecule, or after its incorporation. It is presently preferred that the attaching step be performed on the adenosine derivative prior to its incorporation into the transcribed RNA molecule.

The method can further comprise one or more purification steps after the incubation step. The purification step can involve use of gel electrophoresis (such as polyacrylamide gel electrophoresis; PAGE), membrane filtration, or liquid chromatography. The method can further comprise visualizing and/or quantifying the prepared RNA molecules using fluorescence, phosphorimaging, or other radioimaging methods.

Methods of Use

The above described RNA molecules can be used in a wide array of chemical and biological applications. The RNA molecules can be used for nucleic acid detection, hybridizing to a complementary DNA sequence. The RNA molecules can be used in the designed or random generation of catalytic RNAs. The RNA molecules can be used in antisense applications. The RNA molecules can be used to study the structure and function of RNA sequences. The RNA molecules can be used to investigate interaction between RNA and other biomolecules such as protein and amino acids, polysaccharides and sugars, lipods, coenzymes, nucleotides, and RNA.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Materials

3'-Dephospho coenzyme A (De-P-CoA), NAD, and FAD were purchased from Sigma-Aldrich (St. Louis, Mo.) (Catalog #D3385, N6522, and F6625 for De-P-CoA, NAD, and FAD, respectively). ATP, UTP, GTP, and CTP were from Boehringer Mannheim (Indianapolis, Ind.). RNA polymerase came from Epicentre Technologies (Madison, Wis.). RNase inhibitor, Taq DNA polymerase, nuclease P1, DTT, dATP, dTTP, dGTP, and dCTP were obtained from Promega Life Science Technologies (Madison, Wis.). Thiopropyl Sepharose 6B was from Amersham Pharmacia Biotech (Piscataway, N.J.). DNA oligonucleotides were obtained from either Operon Technologies (Alameda, Calif.) or Integrated DNA Technologies (Coralville, Iowa).

The following chemicals were from Sigma-Aldrich-Fluka (St. Louis, Mo.): Ethylenediamine (EDA), Sigma E4379, 1,6-Hexanediamine (HDA), Sigma H2381, Biotin N-hydroxysuccinimide ester (Biotin-SE), Sigma H1759, 5(6)-Carboxyfluorescein N-hydroxysuccinimide ester [5(6)-FAM-SE], Sigma C1609, N-(3-Dimethylaminopropyl)-N'-ethylcarbodiimide hydrochloride (EDAC), Sigma E7750, 6-Chloropurine riboside, Sigma C8276, 8-(6-Aminohexyl) aminoadenosine 5'-monophosphate lithium salt (8-HDA-AMP), Sigma A3771. 1,4-Butanediamine (BDA), Fluka 32791, 2,2'-Oxydiethylamine dihydrochloride (ODEA), Fluka 75961, 2,2'-(Ethylenedioxy)diethylamine (EDODEA), Fluka 03739, 4,7,10-Trioxa-1,13-tridecanediamine (TOTDDA), Fluka 92892, Phosphorus oxychloride, Fluka 79580, Triethyl phosphate, Aldrich T6110-7.

Example 2

Transcription, DNazyme Cleavage, and Gel Electrophoresis

Transcription promoter sequence was derived from the T7 class II promoter (φ2.5) (FIG. 1) (Dunn, J. J., and Studier, F. W., *J. Mol. Biol.* 166: 477-535 (1983)). The RNA sequence was from a previously isolated coenzyme-synthesizing ribozyme (Huang, F., et al., *Biochemistry* 39: 15548-15555 (2000)), CoES7, with the sequence of 5'-AGGGAAGTGC-TACCACAACUUUAGCCAUAAUGUCACU-UCUGCCGCGGGCAUGCGGCCAGCCA-3' (SEQ ID NO:1). Transcription was carried out under the following standard conditions: 1 mM each of ATP, UTP, GTP, and CTP, 40 mM Tris (pH 8.0), 6 mM $MgCl_2$, 2 mM spermidine, 0.01% Triton X-100, 5 mM DTT, 0.2 unit/mL RNase inhibitor, 0.2 mM DNA templates, and 5 unit/mL T7 RNA polymerase. In addition, different concentrations of coenzymes, De-P-CoA, NAD, and FAD were included to initiate transcription. For quantitation purposes, [$\alpha$-$^{32}$P]ATP (NEN Life Science, Boston, Mass.) was also added to transcription solutions to internally label RNA transcripts. All transcription reactions were allowed to proceed for 2 hours at 37° C. before product analysis by 8% denaturing PAGE.

To physically separate CoA-RNA from pppRNA by PAGE, a different RNA sequence of 35 nucleotides was designed to allow a specific DNazyme (Santoro, S. W. and Joyce, G. F., *Proc. Natl. Acad. Sci. USA* 94: 4262-4266 (1997)) cleavage after transcription. Two DNA oligonucleotides with the sequence of 5'-CAGTAATACGACTCAC-TATTAGGGAAGCGGGCATGCGGCCAGC-CATAGCCGATCA-3' (SEQ ID NO:2) and 5'-TGATCGGCTATGGCTGGCCGCATGCCCG-3' (SEQ ID NO:3) were used to construct (by PCR) a DNA duplex template, from which a 35 nt RNA sequence of 5'-AGG-GAAGCGGGCAUGCGGCCAGCCAUAGCCGAUCA-3' (SEQ ID NO:4) was transcribed. A DNazyme (with the sequence of 5'-TGATCGGCTAGGCTAGCTACAACGAG-GCTGGCCGC-3'; SEQ ID NO:5) was then used to specifically cleave off a portion of the 3' heterogeneous ends of both CoA-RNA and pppRNA, yielding a homogeneous length of 25 nt CoA-RNA and pppRNA. Similar transcription conditions were used with the exception of different concentrations of ATP. Transcribed RNA (about 2 mM) was incubated with 0.4 mM DNazyme for 60 minutes at 37° C. in 50 mM $MgCl_2$ and 50 mM Tris, pH 8.0. RNA was then analyzed by 12% denaturing PAGE.

Example 3

RNA Quantitation

After polyacrylamide gel electrophoresis, individual RNA bands were visualized through phosphorimaging (Molecular Imager, Bio-Rad Laboratories, Hercules, Calif.). Quantitation of different RNA bands was achieved through profile integration after horizontal background subtraction. Coenzyme-RNA (CoE-RNA) yields were calculated based on relative intensity of pppRNA bands (N, N+1, and N+2 bands) in the absence of coenzymes. To confirm the validity of the calculation, DNazyme-cleaved pppRNA and CoA-RNA were quantitated directly after gel resolution of CoA-RNA from pppRNA. In addition, CoA-RNA yield was determined independently by thiopropyl Sepharose 6B affinity chromatography based on its free sulfhydryl group.

Example 4

Fluorescence Emission Spectra of FAD-RNA

FAD-RNA was prepared by transcription under the standard conditions in the presence of 4 mM FAD (no [$\alpha$-$^{32}$P] ATP was added). Two consecutive purification procedures were used to ensure that purified FAD-RNA does not contain free FAD from the transcription solution. After 4 hours of transcription at 37° C., the RNA sample was loaded onto a Microcon filter (M30, Millipore Corp., Bedford, Mass.) and centrifuged at 14,000 g to a final volume of about 5 mL. Next, 200 mL of water was added to the Microcon filter and centrifuged down to about 5 mL solution left on the filter.

Equal volume of gel loading solution containing 7 M urea and 0.02% xylene cyanol was added to the filter. Recovered RNA from the filter was heated at 90° C. for 1 minute and loaded onto an 8% denaturing polyacrylamide gel. After gel electrophoresis, RNA bands (containing both pppRNA and FAD-RNA) were located by UV shadowing and excised from the gel. RNA was then eluted and recovered by ethanol precipitation.

Fluorescence emission spectra of 0.1 mM free FAD and 0.1 mM FAD-RNA (after FAD-RNA yield correction) were recorded with an ISS PC1 fluorometer (ISS Inc., Champaign, Ill.). FAD has two absorption peaks, located at approximately 370 nm and 450 nm (with e450>e370), respectively. Its fluorescence emission spectrum peaks at about 530 nm. When FAD is excited at 450 nm, the Raman scatter peak co-localizes with fluorescence emission peak at about 530 nm. To avoid the interference of the Raman scatter with fluorescence emission, both free FAD and FAD-RNA were excited at 370 nm. To see the effect of RNA on FAD fluorescence emission intensity, FAD-RNA emission spectra were also recorded before and after complete digestion by nuclease P1. Digestion of RNA was achieved by adding 1 unit of nuclease P1 in a buffer containing 10 mM NaAc (pH 5.2) and 0.4 mM $ZnCl_2$. The effect of urea on FAD-RNA fluorescence was also investigated with two different concentrations of urea, 4 M and 7 M.

Example 5

Adenosine Derivative-Initiated Transcription

ATP-initiated transcription (Huang, F., et al., *Biochemistry*, 39: 15548-15555 (2000)) under the T7 class II promoter (Dunn, J. J., and Studier, F. W., *J. Mol. Biol.* 166: 477-535 (1983)) has been previously demonstrated. As an extension of the work, we sought to develop a general transcription method for preparation of RNA with adenosine derivatives linked to its 5' end. Because many biological cofactors, such as coenzymes CoA, NAD, and FAD, contain an adenosine group, they may be used as the transcription initiators under the T7 class II promoter, leading to the synthesis of cofactor-linked RNA. Because CoA contains a 3' phosphate group that can block 3' extension, dephosphorylated CoA (De-P-CoA) must be used to initiate transcription.

Transcription of CoES7 RNA was carried out under the standard conditions, with the addition of various concentrations of coenzymes. After fractionation by PAGE, different RNA bands became clearly visible. In the absence of any coenzymes (lane 1), transcription produced three pppRNA bands in decreasing order: the full-length RNA transcripts (N band), N+1, and N+2 bands (with one and two extra nucleotides added at the 3' end of full-length RNA). Their relative yields were 59%, 35%, and 6% (from N to N+2), respectively. When one of the three coenzymes, De-P-CoA, NAD, and FAD, was added to the transcription solution (lanes 2-4), no additional RNA bands were generated. However, the relative intensity of the three RNA bands in each lane changed considerably when compared with that of lane 1. In all three lanes (lanes 2-4), the intensity of the N band RNA decreased, while both N+1 and N+2 bands were significantly higher than those in lane 1. In the presence of 4 mM De-P-CoA (lane 2), the relative intensity of the three bands changed to 40%, 45%, and 15% (from N to N+2). The relative RNA band intensity were 30%, 49%, and 21% for both NAD- and FAD-initiated transcription (lanes 3 and 4). These changes in RNA band relative intensity resulted from the incorporation of coenzymes (De-P-CoA, NAD, and FAD) into RNA. When one of these coenzymes is incorporated to the 5' end of RNA, the coenzyme-linked RNA (CoE-RNA) behaves as if an extra normal nucleotide is added to the pppRNA. Therefore, the N band CoE-RNA co-migrates with the N+1 band pppRNA, while the N+1 band CoE-RNA and the N+2 band pppRNA run together in the gel. The N+2 band CoE-RNA was barely visible because of its low intensity. To confirm the incorporation of coenzymes into RNA under the class II promoter, three independent experiments were performed: resolution of CoA-RNA from pppRNA by gel after DNazyme cleavage, measurement of free sulfhydryl group of CoA-RNA, and fluorescence emission spectrum of FAD-RNA.

Figure 4A:
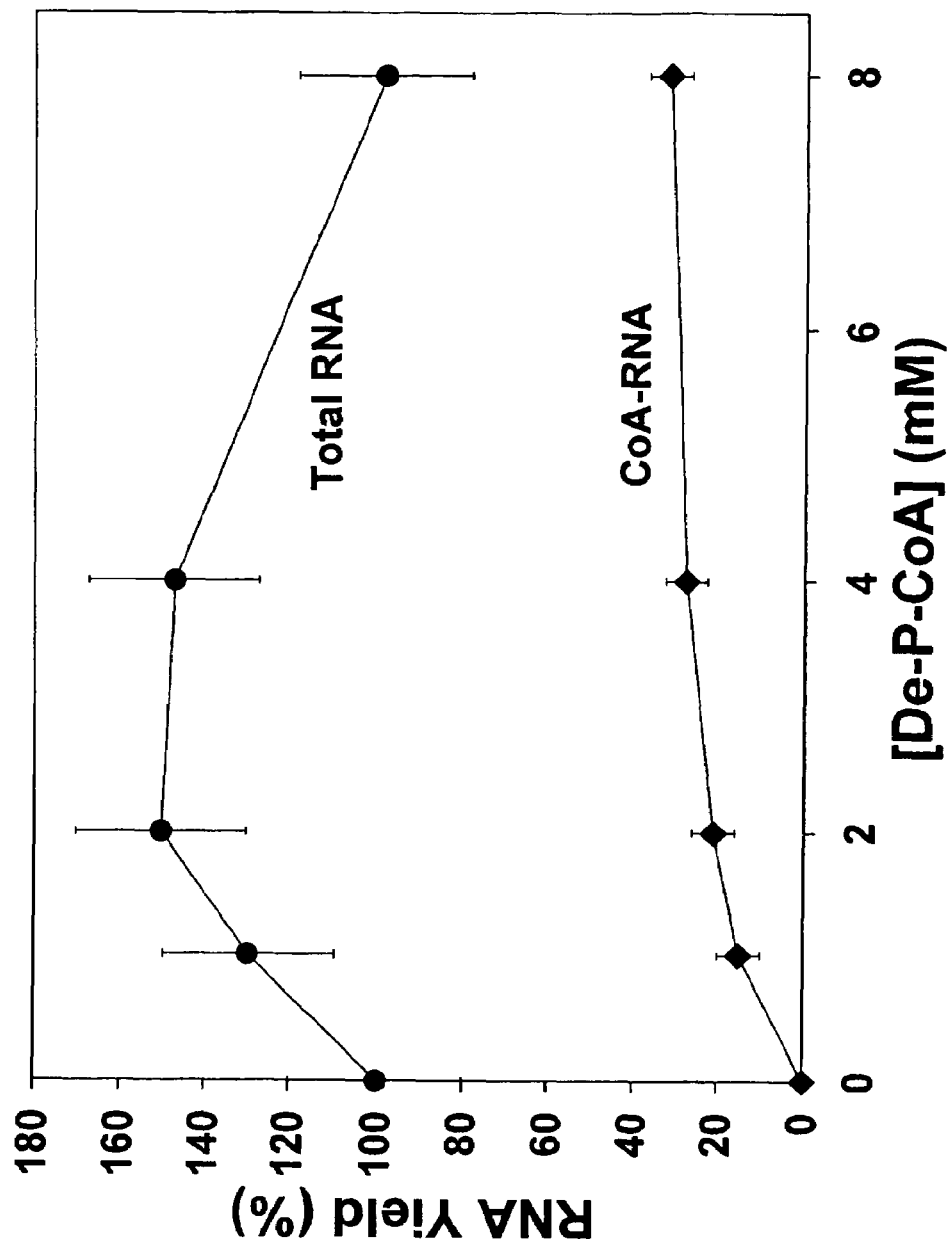
FIGS. 4A-4C shows the concentration effects of RNA transcription in the presence of CoA (FIG. 4A), NAD (FIG. 4B), and FAD (FIG. 4C).
Figure 4B:
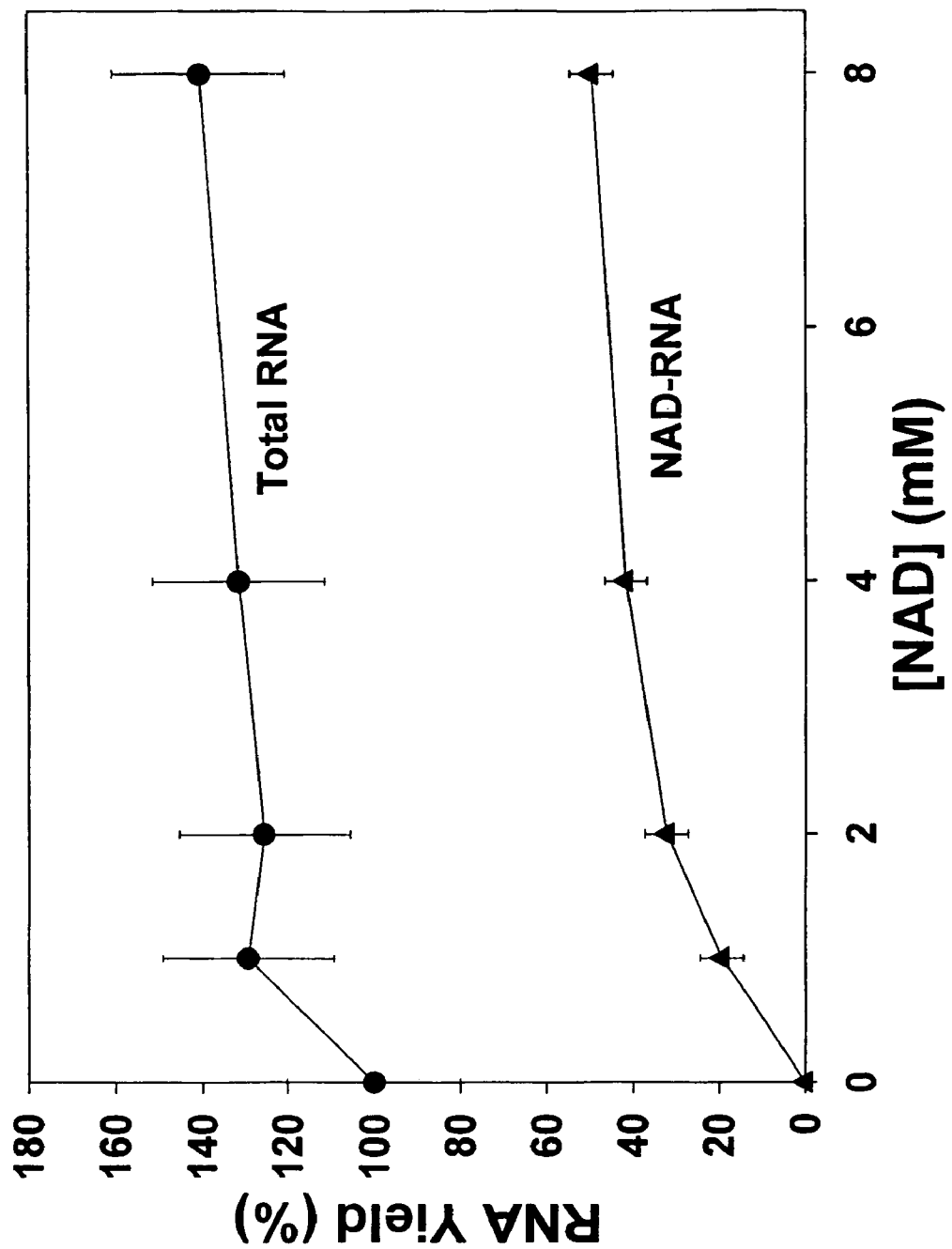
Figure 4C:
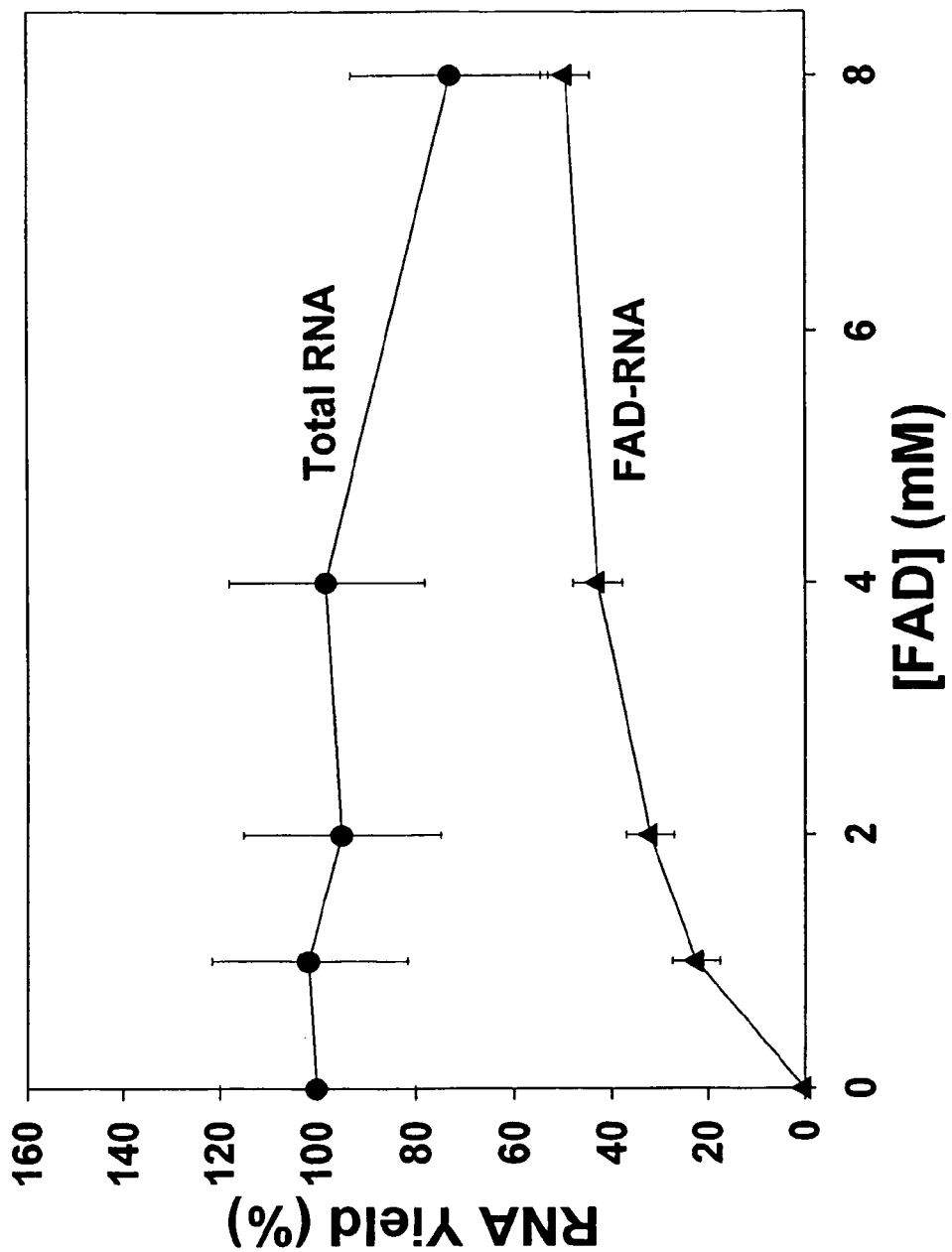
Figure 5:
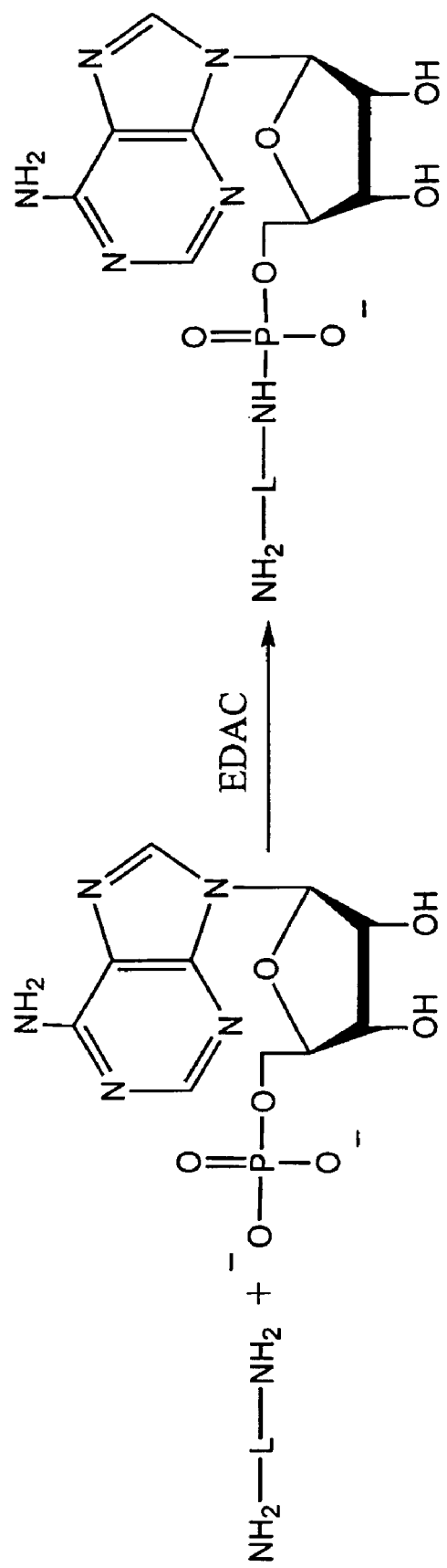
FIG. 5 shows a method of synthesizing adenosine 5'-(ω-amino-linker) phosphoramidate.
Figure 6:
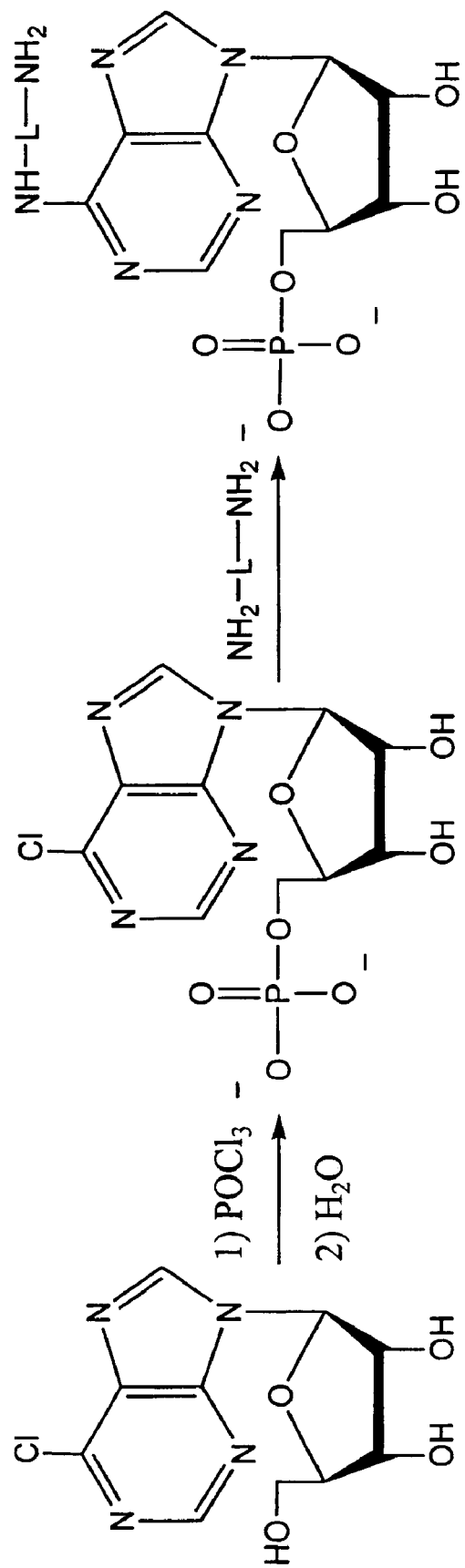
FIG. 6 shows a method of synthesizing N6-(ω-amino-linker) adenosine 5'-monophosphate.

Both the total RNA yields and CoE-RNA yields depend on coenzyme concentrations, as shown in FIGS. 4A-4C. Among the three coenzymes included in this investigation, individual coenzymes appear to have some different effects on transcription. For De-P-CoA incorporation (FIG. 4A), the total RNA yield (pppRNA+CoA-RNA) first increases slightly with the concentration of De-P-CoA, indicating that De-P-CoA stimulates transcription to some extent at low concentrations. However, at higher concentrations, the stimulatory effect of De-P-CoA disappears, and eventually becomes inhibitory. On the other hand, the CoA-RNA yield increases when higher concentrations of De-P-CoA are added to the transcription solution. CoA-RNA reaches 30-35% of total RNA synthesized at 4-8 mM De-P-CoA. Both NAD and FAD have a similar effect on relative CoE-RNA yields (FIGS. 4B and 4C). NAD-RNA and FAD-RNA first increase rapidly with the concentration of NAD and FAD, and then plateau at high NAD and FAD concentrations. In the presence of 4-8 mM NAD or FAD, transcription produces 35-40% NAD-RNA or FAD-RNA over the total RNA synthesized. On the other hand, NAD and FAD appear to exert different effects on total RNA yields. While different concentrations of NAD slightly stimulate transcription (FIG. 4B), FAD appears to have somewhat inhibitory effect, especially at high concentrations (>4 mM) (FIG. 4C). Results in FIGS. 4A-4C were derived from two independent transcription experiments. The relative CoE-RNA yields in FIGS. 4A-4C are very reproducible. However, some degree of variation in total RNA yields may exist among different experiments. In the presence of higher than 8 mM coenzymes (especially De-P-CoA and FAD), total RNA yields can be significantly lower than under the standard transcription conditions.

Example 6

Resolution of Coenzyme-RNA From pppRNA

To physically resolve coenzyme-RNA from pppRNA by gel, a DNazyme (Santoro, S. W., and Joyce, G. F., *Proc. Natl. Acad. Sci. USA*, 94: 4262-4266 (1997)) was designed to trim off the 3' heterogeneous ends of RNA. Although transcription produces N, N+1, and N+2 bands of both pppRNA and CoA-RNA, the DNazyme cuts at a specific site and yields both CoA-RNA and pppRNA of the same length of 25 nt. Comparing lanes 1 and 2, the upper band in lane 2 represents CoA-RNA (33%), while the bottom band is pppRNA (it is not clear why there was a weak band above the expected product bands, but it represented well below 10% of total RNA). The CoA-RNA yield agrees well (within the experimental error of 5%) with the results from FIG. 4A. When the concentration of De-P-CoA was maintained at 4 mM and the ATP concentration was reduced from 1 mM to 0.5 mM, 0.2 mM, and 0.1 mM (keeping GTP, CTP, and UTP concentrations at 1 mM), the relative CoA-RNA yield increased from 33% to 46%, 52%, and 56%. On the other hand, the total RNA yield decreased from 110% (relative to the RNA obtained at 1 mM ATP and 0 mM De-P-CoA) to 85%, 44%, and 12%. The seemingly more intense bands in lanes 3 & 4 relative to lane 2 resulted from higher ratios of [$\alpha$-$^{32}$P] ATP/ATP when ATP concentration was lowered.

The effect of 3' blocked adenosine derivatives on transcription was also investigated by gel after DNazyme cleavage of RNA. At 4 mM, neither CoA nor 3' AMP has detectable effect on either normal RNA transcription (with no coenzymes) or CoA-RNA transcription (in the presence of 4 mM De-P-CoA). The result is in excellent accordance with the specific adenosine derivative-initiated transcription, which requires a free 3' hydroxyl group for RNA extension.

To further confirm the yields of CoE-RNA derived from PAGE and phosphorimaging analysis, the CoA-RNA yield was independently determined through its 5' free sulfhydryl group by thiopropyl Sepharose 6B affinity chromatography. CoES7 RNA was prepared under 1 mM ATP and 4 mM De-P-CoA and purified by membrane filtration with Microcon 30. After passing the RNA through a thiopropyl Sepharose 6B column followed by thorough washing with water, 30-35% of loaded RNA was retained. The retained RNA was completely released from the column by 30 minutes incubation with 20 mM DTT in 20 mM Tris, pH 8.5. The result not only confirms that CoA-RNA is synthesized by T7 RNA polymerase in the presence of De-P-CoA but also corroborates quantitatively the results from PAGE and phosphorimaging analysis. Further confirmation of CoE-RNA synthesis comes from the following fluorescence measurement of FAD-RNA.

Example 7

Fluorescence Emission Spectra

Fluorescence emission spectra of purified FAD-RNA (CoES7) and free FAD were determined. Except for lower fluorescence intensity of FAD-RNA relative to that of free FAD, both spectra are similar, with no apparent spectral shift. At the same concentration, fluorescence intensity of FAD-RNA is about 35-40% of that of free FAD in 20 mM MES, pH 6.0. This decrease in fluorescence of FAD upon covalent coupling to RNA is presumably due to quenching by FAD-linked RNA, because similar concentrations of RNA added to free FAD solutions (0.1 mM) do not affect the fluorescence emission of FAD.

To demonstrate the effect of covalent linkage to RNA, emission spectra of FAD-RNA were taken before and after complete digestion of FAD-RNA by nuclease P1. Although no spectral shift was observed, fluorescence intensity increased 2.5 fold to the level of free FAD. This result confirms that covalent linkage to RNA considerably reduces the fluorescence quantum yield of FAD.

The effect of covalent coupling to RNA can be further demonstrated through FAD-RNA denaturation by urea. High concentrations of urea significantly increase the fluorescence intensity of FAD-RNA. In 4 M and 7 M urea (containing 0.5 M sodium acetate, pH 5.2), fluorescence intensity of FAD-RNA was enhanced 2.5 and 5.1 fold, respectively. On the other hand, free FAD's fluorescence increased only 1.7 and 2.7 fold under the same conditions.

These results suggest that the reduced fluorescence of FAD-RNA relative to that of free FAD is not a result of the covalent linkage itself between FAD and the 5' end of RNA. The fluorescence decrease is rather caused by folded RNA conformation. In free FAD, stacking between the isoalloxazine and the adenine significantly quenches the fluorescence intensity of isoalloxazine (Bessey, O. A., et al., *J. Biol. Chem.* 180: 755-769 (1949); Weber, G., *Biochem. J.* 47: 114-121 (1950)). In the presence of 7 M urea, unstacking of the isoalloxazine and the adenine of free FAD results in a fluorescence enhancement of 2.7 fold. Under the same conditions, FAD-RNA is denatured (both RNA conformation and the stacking of the isoalloxazine and the adenine of FAD moiety), leading to a 5.1 fold increase in fluorescence intensity. The larger increase in fluorescence intensity of FAD-RNA over free FAD in the presence of 7 M urea reflects the contribution of the folded RNA conformation, which is corroborated by the 2.5-fold fluorescence reduction from free FAD to FAD-RNA. Both FAD and FAD-RNA exhibit similar fluorescence quantum yields (same fluorescence intensity from same concentrations of FAD and FAD-RNA) in 7 M urea, indicating that the isoalloxazine group in FAD and FAD-RNA is in similar chemical environment under these conditions. Thus, introducing the covalent bond by itself between FAD and RNA does not appear to affect FAD fluorescence. However, the covalent linkage is necessary to bridge the interaction between FAD and RNA, because similar RNA concentrations added to free FAD solutions do not affect FAD fluorescence intensity.

Example 8

Synthesis of 5' Amino-Derivatives of Adenosine Phosphoramidate

Direct coupling of diamines with AMP (Chu, B. C., et al., *Nucleic Acids Res.* 11: 6513-6529 (1983)) by the water-soluble carbodiimide, EDAC, was used to synthesize a series of six 5' amino-derivatives of adenosine phosphoramidate, which differ by the linker length. The reactions and structures are shown in FIG. 1. Briefly, 0.25 μmol of AMP and 5.0 μmol of one of the 6 diamines (ethylenediamine, 1,4-butanediamine, 1,6-hexanediamine, 2,2'-oxydiethylamine, 2,2'-(ethylenedioxy)diethylamine, and 4,7,10-trioxa-1,13-tridecanediamine) were dissolved in 1.0 mL water. The solution pH was adjusted to 6.0-6.5 with 6 N HCl. Solid EDAC (hydrochloride, 1.5 μmol) was then added to the AMP-diamine mixture and the reaction was allowed to proceed for 2 hours at room temperature with constant stirring. Product yields were determined by reverse phase HPLC analysis under the following eluting conditions (column, Alltech Expedite C18, 10×4.6 mm and follow rate, 1 mL/minute): 5% MeOH/95% 20 mM phosphate (pH 7.0) for AMP with EDA the reactions; 10% MeOH/90% 20 mM phosphate (pH 7.0) for the reactions of AMP with BDA, HDA, ODEA, and EDODEA; 15% MeOH/85% 20 mM phosphate for the AMP and TOTDDA reaction.

A semi-preparative HPLC column (Waters Delta Pak C18, 300×7.8 mm) was used to purify all six 5' amino-derivatives of adenosine phosphoramidate. For each product purification, the column was first equilibrated in 100% water. All of the reaction mixture (1-2 mL) was loaded onto the column, followed by washing with about 30 mL of water. The pure product was then eluted with 30% MeOH. Collected product solutions were concentrated under vacuum to a final volume of about 0.5 mL. Concentrations of purified 5' amino-derivatives of adenosine phosphoramidate were determined by their absorbance at 260 nm, using a molar extinction coefficient of 15,000 $M^{-1}$ $cm^{-1}$.

Example 9

Synthesis of N6-Amino-Derivatives of Adenosine 5' Monophosphate

A series of six N6 amino-derivatives of AMP were synthesized by diamine-displacement of 6-chloropurine riboside 5' monophosphate, which was prepared by phosphorylation of 6-chloropurine riboside with phosphorus oxychloride: To 7.7 ml of triethylphosphate, 3 mmol of 6-chloropurine riboside was suspended at 0° C. Small fractions of phosphorus oxychloride (0.56 mL, 6 mmol) were added over a period of 30 minutes with constant stirring. The suspension was kept stirring at 0° C. for additional 1.5 hours, when the white suspension became clear solution. Water (2 mL) was added to hydrolyze the 5' phosphoryl chloride to 5' monophosphate. The solution was then neutralized to pH 5 by NaOH. HPLC analysis (Alltech Expedite C18, 10×4.6 mm; 10% MeOH/90% 20 mM phosphate; and follow rate, 0.5 mL/minute) indicated near complete conversion of 6-chloropurine riboside to 6-chloropurine riboside 5' monophosphate. The reaction mixture was directly used for the synthesis of the following N6 amino-derivatives of AMP.

To 0.1 mmol of the above 6-chloropurine riboside 5' monophosphate solution, 1 mmol of diamines (EDA, BDA, HDA, ODEA, EDODEA, TOTDDA in their free amine state) was added. After stirring at room temperature for 30 minutes, the solution was acidified to pH 3.5 by HCl. HPLC analysis [Alltech Expedite C18, 10×4.6 mm; 100%-70% ammonium formate (pH 3.2) and 0-30% MeOH; follow rate, 0.5 mL/minute] indicated 60-90% conversion of 6-chloropurine riboside 5' monophosphate to N6-amino-derivatives of AMP.

Products were purified by semi-preparative HPLC under the following conditions: Waters Delta Pak C18, 300×7.8 mm; follow rate, 2 mL/minute. The reaction mixture was loaded onto the column pre-equilibrated with 20 mM ammonium formate (pH 3.2). Products were eluted with 30-50% MeOH. Collected product solutions were concentrated under vacuum and re-injected back onto the semi-preparative column that was equilibrated in 100% water. After washing with 2030 mL of water, the product was eluted with 50% MeOH. After concentration of collected product fractions, their concentrations were determined by absorbance at 267 nm ($\epsilon_{267}=18,500 M^{-1} cm^{-1}$).

Example 10

Synthesis of 5' and N6-Fluorescein Derivatives of Adenosine Phosphoramidate and AMP Fluorescein-tagged nucleotides of 5'- and N6-amino-derivatives of adenosine phosphoramidate and AMP were prepared by reacting these 5'- and N6-amino-derivatives with 5(6)-carboxyfluorescein N-hydroxysuccinimide ester [5(6)-FAM SE] as following: mixing 5 μL of 0.4 M amino-derivatives of adenosine phosphoramidate and AMP and 5 μL of 1 M NaHCO₃ (pH 8.0) with 10 μL of 0.2 M 5(6)-FAM SE solution (freshly made in DMSO). The reaction mixture was incubated for 30 minutes at room temperature. HPLC analysis (Alltech Expedite C18, 10×4.6 mm; 30%-40% MeOH & 70%-60% 20 mM KH₂PO₄, pH 4.6) showed 70 90% fluorescein conversion to a pair (5 and 6) of fluorescein-tagged nucleotides.

Purification was performed by HPLC under the following conditions: loading all the reaction solution in 25-40% MeOH and 75-60% KH₂PO₄. After 15-30 min, MeOH concentration was increased by 5%. Two fractions containing fluorescein nucleotides from the elution were collected and concentrated under vacuum. Their concentrations were determined by absorbance at 492 nm in 20 mM phosphate buffer (pH 7.0), $\epsilon_{492}=82,000 M^{-1} cm^{-1}$.

Example 11

Synthesis of 5' and N6-Biotin Derivatives of AMP

Seven biotinyl compounds of 5'- and N6-amino-derivatives of adenosine phosphoramidate and AMP were prepared by reaction of biotin N-hydroxysuccinimide ester with the amino derivatives. To a mixture of 20 μL of 0.4 M amino-derivative of adenosine phosphoramidate or AMP and 10 μL of 1 M NaHCO₃, 20 μL of freshly made 0.2 M biotin-NHS solution (in DMSO) was added. The reaction mixture was allowed to incubate for 30 minutes at room temperature. HPLC analysis (Alltech Expedite C18, 10×4.6 mm; 30% MeOH/70% 20 mM KH₂PO₄, pH 4.6) showed 40-60% conversion of amino-derivatives of adenosine phosphoramidate and AMP to biotin-tagged nucleotides.

Purification was performed by HPLC under the following conditions: loading all the reaction sample onto a Waters Delta Pak C18, 150×3.9 mm, equilibrated in 100% water. After 5-10 minutes, the mobile phase was changed to 15-20% MeOH. One major fraction containing the product biotinyl nucleotide was eluted. After another 5-10 minutes, MeOH concentration was increased to 35-40%. Another major fraction containing the desired product was eluted. Collected biotin nucleotide solutions were concentrated and their concentrations were determined by absorbance at 260 nm, using $\epsilon_{260}=15,000 M^{-1} cm^{-1}$.

Example 12

Incorporation of 5'- and N6-Amino, Fluorescein, and Biotin Derivatives into RNA by In Vitro Transcription For all RNA transcription experiments, the promoter sequence was derived from the T7 class II promoter (Dunn, J. J. and Studier, F. W. *J. Mol. Biol.*, 166: 477-535 (1983); Huang, F. *Nucleic Acids Res.* 31: e8 (2003)). The RNA sequence was a 35 mer used in previously transcription studies (Huang, F. *Nucleic Acids Res.* 31: e8 (2003)): 5'-AGGGAAGCGGGCAUGCGGCCAGC-CAUAGCCGAUCA-3' (SEQ ID NO:4). Transcription was carried out under the following conditions (final concentrations): 1 mM each of UTP, GTP, and CTP, 0.25 mM ATP, 40 mM Tris (pH 8.0), 6 mM MgCl₂, 2 mM spermidine, 0.01% Triton X-100, 5 mM DTT, 0.2 μM DNA templates, and 5 unit/μL T7 RNA polymerase. In addition, different concentrations of a transcription initiator (5'-amino derivatives of adenosine phosphoramidate, N6-amino derivatives of AMP, or their fluorescein and biotin derivatives) was added. The radiolabel, [α-³²P]ATP (NEN Life Science, Boston, Mass.), was also included to transcription solutions to internally label RNA transcripts. All transcription reactions were incubated for 2 h at 37° C. before product analysis by 8% denaturing PAGE.

Example 13

Posttranscriptional Fluorescein Labeling of 5' Amino-RNA

Fluorescein labeling of 5' $NH_2$-linker-RNA (prepared above as internally $^{32}P$-labeled RNA) was achieved by reaction with 5(6) carboxyfluorescein-NHS in a total volume of 2 μL containing 0.5 M $NaHCO_3$ and 0.1 M carboxyfluorescein-NHS (freshly prepared in DMSO). Reactions were incubated for 30 minutes at room temperature. A gel-loading dye solution (8 μL) was then added, and 1 μL of samples was loaded onto an 8% denaturing gel for analysis.

Example 14

RNA Quantitation

After polyacrylamide gel electrophoresis, the intensity of individual RNA bands were quantitated through phosphorimaging (Molecular Imager, Bio-Rad Laboratories, Hercules, Calif.). Different RNA bands were analyzed through profile integration after horizontal background subtraction. Derivatized RNA (5'-amino, fluorescein, and biotin) yields were calculated based on relative intensity of pppRNA bands (N, N+1, and N+2 bands) in the absence of AMP derivatives. To confirm the results of the calculation, 5'-biotin-labeled RNA yields were determined independently by streptavidin gel shift assay.

Example 15

Coupling of Amino Acids, Peptides, and Proteins to Transcribed RNA Molecules The free terminal primary amine group of the adenosine 5'-(ω-amino-linker) phosphoramidate and the N6-(ω-amino-linker) adenosine 5'-monophosphate (VI) can be used to covalently attach amino acids, peptides, and proteins to the transcribed RNA molecules. Standard peptide synthesis chemistries can be used to form a covalent amide bond between the amino group and a carboxylate group present in the amino acid, peptide, or protein. Example chemistries useful for forming amide bonds include HBTU/HOBT, HATU/HOAT, PyBOP/HOBT, and OPFP preactivated amino acids/HOBT.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:

1. A method for the preparation of a RNA molecule containing an adenosine derivative covalently attached at the 5' end of the RNA molecule, the method comprising:
   providing a DNA template comprising a T7 class II RNA polymerase promoter sequence, wherein the promoter sequence is SEQ ID NO:7;
   contacting the DNA template with T7 RNA polymerase enzyme, an adenosine derivative, ATP, UTP, GTP, and CTP to prepare a reaction mixture; and
   incubating the reaction mixture under conditions suitable for RNA transcription to prepare the RNA molecule containing an adenosine derivative covalently attached at the 5' end.

2. The method of claim 1, wherein the adenosine derivative is a 5' derivative of adenosine or an N6 derivative of adenosine.

3. The method of claim 1, wherein the adenosine derivative is coenzyme A dephosphorylated at the 3' position (De-P-CoA), FAD, NAD, S-(5'-adenosyl)-cysteine, S-(5'-adenosyl)-homocysteine, or S-(5'-adenosyl)-methionine.

4. The method of claim 1, wherein the adenosine derivative is adenosine 5'-O-thiomonophosphate, adenosine 5'-[β-thio]diphosphate, adenosine 5'-[γ-thio]triphosphate, adenosine 5'-(α,β-methylene)diphosphate, adenosine 5'-(β,γ-imido)triphosphate, adenosine 5'-triphosphate γ-(1-(2-nitrophenyl)ethyl) ester, or 5'-p-fluorosulfonylbenzoyladenosine.

5. The method of claim 1, wherein the adenosine derivative is a fluorescein derivative of adenosine, a biotin derivative of adenosine, an Alexa derivative of adenosine, a BODIPY derivative of adenosine, a Cy3 derivative of adenosine, or a Cy5 derivative of adenosine.

6. The method of claim 1, wherein the adenosine derivative is covalently attached to an amino acid, a peptide, a neurotransmitter, an amino acid-sugar, or a protein.

7. The method of claim 1, further comprising purifying the RNA molecule after the incubating step.

8. The method of claim 1, wherein the reaction mixture further comprises at least one radiolabel selected from the group consisting of $[\alpha\text{-}^{32}P]ATP$, $[\alpha\text{-}^{32}P]GTP$, $[\alpha\text{-}^{32}P]CTP$, $[\alpha\text{-}^{32}P]UTP$, $[\alpha\text{-}^{35}S]ATP$, $[\alpha\text{-}^{35}S]GTP$, $[\alpha\text{-}^{35}S]CTP$, and $[\alpha\text{-}^{35}S]UTP$.

* * * * *

SEQUENCE LISTING

```
<160> NUMBER OF SEQ ID NOS: 9

<210> SEQ ID NO 1
<211> LENGTH: 62
<212> TYPE: DNA
<213> ORGANISM: Artificial
<220> FEATURE:
<223> OTHER INFORMATION: Isolated from randomized sequence library.

<400> SEQUENCE: 1
agggaagtgc taccacaacu uuagccauaa ugucacuucu gccgcgggca ugcggccagc      60
ca                                                                    62

<210> SEQ ID NO 2
<211> LENGTH: 55
<212> TYPE: DNA
<213> ORGANISM: Artificial
<220> FEATURE:
<223> OTHER INFORMATION: Designed to allow DNazyme cleavage after
      transcription.

<400> SEQUENCE: 2
cagtaatacg actcactatt agggaagcgg gcatgcggcc agccatagcc gatca          55

<210> SEQ ID NO 3
<211> LENGTH: 28
<212> TYPE: DNA
<213> ORGANISM: Artificial
<220> FEATURE:
<223> OTHER INFORMATION: Designed to allow DNazyme cleavage after
```

```
                              transcription.

<400> SEQUENCE: 3
tgatcggcta tggctggccg catgcccg                                    28

<210> SEQ ID NO 4
<211> LENGTH: 35
<212> TYPE: RNA
<213> ORGANISM: Artificial
<220> FEATURE:
<223> OTHER INFORMATION: RNA transcribed from SEQ ID NO:2.

<400> SEQUENCE: 4
agggaagcgg gcaugcggcc agccauagcc gauca                            35

<210> SEQ ID NO 5
<211> LENGTH: 35
<212> TYPE: DNA
<213> ORGANISM: Artificial
<220> FEATURE:
<223> OTHER INFORMATION: Isolated from randomized sequence library.

<400> SEQUENCE: 5
tgatcggcta ggctagctac aacgaggctg gccgc                            35

<210> SEQ ID NO 6
<211> LENGTH: 23
<212> TYPE: DNA
<213> ORGANISM: Bacteriophage T3

<400> SEQUENCE: 6
aattaaccct cactaaaggg aga                                         23

<210> SEQ ID NO 7
<211> LENGTH: 22
<212> TYPE: DNA
<213> ORGANISM: Bacteriophage T7

<400> SEQUENCE: 7
taatacgact cactattagg ag                                          22

<210> SEQ ID NO 8
<211> LENGTH: 23
<212> TYPE: DNA
<213> ORGANISM: Bacteriophage SP6
<220> FEATURE:
<221> NAME/KEY: misc_feature
<222> LOCATION: (22)..(22)
<223> OTHER INFORMATION: n is a, c, g, or t

<400> SEQUENCE: 8
atttaggtga cactatagaa gng                                         23

<210> SEQ ID NO 9
<211> LENGTH: 22
<212> TYPE: DNA
<213> ORGANISM: Bacteriophage T7

<400> SEQUENCE: 9
ctcctaatac tgagtcgtat ta                                          22
```